United States Patent
Dube et al.

(10) Patent No.: US 11,780,804 B2
(45) Date of Patent: *Oct. 10, 2023

(54) TRICYANOHEXANE PURIFICATION METHODS

(71) Applicant: Ascend Performance Materials Operations LLC, Houston, TX (US)

(72) Inventors: Sanjay Dube, Madison, AL (US); Darrick Elmore, Pensacola, FL (US)

(73) Assignee: Ascend Performance Materials Operations LLC, Houston, TX (US)

( * ) Notice: Subject to any disclaimer, the term of this patent is extended or adjusted under 35 U.S.C. 154(b) by 560 days.

This patent is subject to a terminal disclaimer.

(21) Appl. No.: 16/880,717

(22) Filed: May 21, 2020

(65) Prior Publication Data

US 2020/0369602 A1 Nov. 26, 2020

Related U.S. Application Data

(60) Provisional application No. 62/852,604, filed on May 24, 2019.

(51) Int. Cl.
C07C 253/34 (2006.01)

(52) U.S. Cl.
CPC .................... *C07C 253/34* (2013.01)

(58) Field of Classification Search
CPC .................................................. C07C 253/34
See application file for complete search history.

(56) References Cited

U.S. PATENT DOCUMENTS

| 3,844,911 | A | 10/1974 | Ruehlen |
| 5,039,436 | A | 8/1991 | Adams |
| 6,018,072 | A * | 1/2000 | Nishihira ............... C07C 69/34 560/146 |
| 7,230,112 | B2 | 6/2007 | Adelman et al. |
| 7,262,256 | B2 | 8/2007 | Date et al. |
| 11,560,353 | B2 * | 1/2023 | Dube .................... C07C 253/34 558/435 |
| 2005/0010021 | A1 * | 1/2005 | Date ...................... C08G 59/00 528/365 |
| 2013/0157119 | A1 | 6/2013 | Shimura et al. |

FOREIGN PATENT DOCUMENTS

| EP | 1460054 A1 | 9/2004 |
| JP | 2003-183239 A | 7/2003 |
| JP | 2003-192631 A | 7/2003 |

* cited by examiner

*Primary Examiner* — Joseph K McKane
*Assistant Examiner* — David M Shim
(74) *Attorney, Agent, or Firm* — COZEN O'CONNOR (57) ABSTRACT

Provided herein are processes for purifying TCH in a feed stream, such as an adiponitrile process stream. The processes include a first separating step of separating the adiponitrile process stream to form a first overhead stream comprising low-boiling components and high-boiling components and a first bottoms stream comprising high-boiling components. The processes also include a second separating step of separating the first overhead stream in one or more distillation columns to form a lights stream comprising low-boiling components, a heavies stream comprising high-boiling components, and a TCH stream.

17 Claims, 5 Drawing Sheets

TRICYANOHEXANE PURIFICATION METHODS

CROSS REFERENCE TO RELATED APPLICATIONS

This application claims priority to U.S. provisional patent application No. 62/852,604, filed May 24, 2019, which is incorporated herein by reference in its entirety.

FIELD

The present disclosure relates generally to production of tricyanohexane (TCH) via purification of by-product or co-product streams of industrial processes. More specifically, the present disclosure relates to processes for recovering TCH present in streams resulting from the production of adiponitrile.

BACKGROUND

Cyanocarbons, e.g., organic compounds having cyano functional groups, are known and are widely used in various applications. Many of these compounds, including acrylonitrile and adiponitrile, are used as monomers to prepare various polymers, such as nylon, polyacrylonitrile, or acrylonitrile butadiene styrene. Adiponitrile, in particular, can be hydrogenated to 1,6-diaminohexane for the production of nylon-6,6. Several methods of producing cyanocarbons are known in the art. For example, a conventional method of producing adiponitrile is the electrohydrodimerization of acrylonitrile, as described in U.S. Pat. No. 3,844,911. This and other production methods often yield streams comprising small amounts of desirable co-products and/or by-products. Typically these streams are treated as waste streams, e.g., burned, but it has been found that repurposing the streams would be preferable in light of the co-product and/or by-products present therein. For example, some of the conventional streams of adiponitrile production processes may contain TCH. TCH has a number of uses, including as a precursor for a number of industrial products or as an additive in lithium ion battery applications.

The usefulness of TCH is described in a variety of references. One example is U.S. Pat. No. 7,262,256, which discloses a polycarboxylic acid mixture comprising 80% by weight or more of 1,3,6-hexanetricarboxylic acid, wherein the polycarboxylic acid mixture has a psychometric lightness L-value of 98 or more, a psychometric chroma a-value of from −2.0 to 2.0 and a psychometric chroma b-value of from −2.0 to 3.0, and has a nitrogen content of 5,000 ppm by weight or less. In particular, the polycarboxylic acid mixture is obtained from a hydrolysis reaction mixture obtained by hydrolyzing a nitrile mixture comprised mainly of 1,3,6-tricyanohexane.

Another example is U.S. Pat. No. 5,039,436, which discloses coupled polyamine additives for lubricants, fuels and functional fluids. The coupled polyamines are prepared by the cyclization reaction of at least one reactant polyamine reactant with at least one hydrocarbyl polynitrile. This coupled polyamine may be further reacted with a hydrocarbyl carboxylic acid or derivative thereof, a hydrocarbyl phenolic reactant or mixtures thereof to provide an additive having greater oil solubility as well as imparting dispersancy and VI improvement. In particular, examples of suitable polynitrile reactants according to the reference include adiponitrile, alpha-methyleneglutaronitrile, 3,3'-iminodipropionitrile, 1,3,6-tricyanohexane and the like.

Another example is U.S. Pat. No. 7,230,112, which discloses a catalytic process for making amide acetals from nitrites and diethanolamines. Amide acetals can be further crosslinked by hydrolyzing the amide acetal groups, and subsequently reacting the hydroxyl groups and/or the amine functions that are formed, to crosslink the composition. In particular, a catalytic process for making amide acetals from 1,3,6,-hexanetricarbonitrile is disclosed.

Another example is U.S. Publication No. 2013/0157119, which discloses a secondary battery in which decomposition of an electrolyte liquid is suppressed and generation of a gas is reduced, even in the case of using a laminate film as a package. The secondary batteries disclosed therein are of the stacked laminate type and comprise an electrode assembly in which a positive electrode and a negative electrode are arranged to face each other, an electrolyte liquid and a package accommodating the electrode assembly and said electrolyte liquid, wherein the negative electrode is formed by binding a negative electrode active substance comprising a metal (a) capable of being alloyed with lithium, a metal oxide (b) capable of occluding and releasing lithium ions and a carbon material (c) capable of occluding and releasing lithium ions, to a negative electrode current collector, with at least one selected from polyimides and polyamideimides, and the electrolyte liquid comprises a predetermined nitrile compound. In particular, electrolyte liquids containing 1,3,6-hexanetricarbonitrile are disclosed.

In view of these and other conventional uses for TCH, the need exists for a cost-effective method of purifying TCH produced in industrial processes. In particular, the need exists for a method of purifying TCH formed during the industrial production of adiponitrile.

SUMMARY

According to one embodiment, the present disclosure relates to a process for purifying TCH, the process including: a first separating step of separating an adiponitrile process stream to form a first overhead stream including low-boiling components and high-boiling components and a first bottoms stream including high-boiling components and solid impurities; and a second separating step of separating the first overhead stream in one or more distillation columns to form a lights stream including low-boiling components, a heavies stream including high-boiling components, and a TCH stream including TCH and less than 10 wt. % impurities, wherein the residence time in an individual column is less than 8 hours. In some aspects, the first overhead stream comprises from 0 wt. % to 20 wt. % heavies. In some aspects, the TCH stream comprises less than 1 wt. % impurities. In some aspects, the TCH stream comprises TCH, from 0 wt. % to 0.05 wt. % adiponitrile, from 0 wt. % to 0.1 wt. % di(2-cyanoethyl) amine, from 0 wt. % to 0.05 wt. % cyanovaleramide, and from 0 wt. % to 0.05 wt. % tri(2-cyanoethyl) amine. In some aspects, the residence time of the first overhead stream in temperatures above 230° C. is less than 8 hours. In some aspects, the residence time of the first overhead stream in pressures above 50 torr is less than 8 hours. In some aspects, the process further comprises recycling at least a portion of the heavies stream, optionally comprising from 0 wt. % to 40 wt. % high-boiling components.

In some aspects, the second separating step further comprises: separating the first overhead stream in a distillation column to form the lights stream as a second overhead stream and a second bottoms stream; and separating the second bottoms stream in a distillation column to form the heavies stream as a third bottoms stream and the TCH stream as a third overhead stream. In some of these aspects, the process further comprises recycling at least a portion of the third bottoms stream. In some of these aspects, the recycling comprises recycling at least a portion of the third bottoms stream to the second bottoms stream and/or to the first overhead stream. In some of these aspects, the recycled stream comprises from 0 wt. % to 40 wt. % high-boiling components. In some of these aspects, the recycling controls the concentration of high-boiling components in the first overhead stream to be from 0 wt. % to 10 wt. %.

In some aspects, the process further comprises a treating step of treating the TCH stream to form a purified TCH stream. In some of these aspects, the treating step comprises nitrogen stripping or treating with a molecular sieve. In some of these aspects, the purified TCH stream comprises less than 0.1 wt. % impurities, less than 20 ppm water, and/or less than 5 ppm metals.

In some aspects, the first separating step comprises flashing the adiponitrile stream or treating the adiponitrile stream in a wiped film evaporator. In some aspects, less than 50 wt. % of high-boiling components in the first overhead stream decompose into low-boiling components during the second separating step. In some aspects, the adiponitrile process stream is a co-product stream produced by an adiponitrile production and/or an adiponitrile purification process. In some of these aspects, the first bottoms stream and/or the lights stream is recycled to the adiponitrile production and/or the adiponitrile purification process.

According to another embodiment, the present disclosure relates to a process for purifying TCH, the process comprising: a first separating step of flashing an adiponitrile process stream to form a first overhead stream comprising low-boiling components and high-boiling components, and a first bottoms stream comprising high-boiling components and solid impurities; a second separating step of distilling the first overhead stream to form a second overhead stream comprising low-boiling components, and a second bottoms stream comprising TCH and heavies; a third separating step of distilling the second bottoms stream to form a third distillate comprising TCH and less than 5 wt. % impurities, and a third bottoms stream comprising heavies; wherein the residence time in the second or third separating step is less than 8 hours. In some aspects, at least a portion of third bottoms stream and/or the second bottoms stream is recycled. In some of these aspects, the recycled stream comprises from 0 wt. % to 40 wt. % heavies.

According to another embodiment, the present disclosure relates to a process for purifying TCH, the process comprising a first separating step of flashing an adiponitrile process stream to form a first overhead stream comprising low-boiling components and high-boiling components, and a first bottoms stream comprising high-boiling components; a second separating step of distilling the first overhead stream to form a second overhead stream comprising low-boiling components, a second bottoms stream comprising heavies, and a side draw comprising TCH and lights; a third separating step of flashing the side draw in a second flash vessel to form a third bottoms stream comprising TCH and less than 5 wt % impurities wherein the residence time in the second or third separating step is less than 8 hours. In some aspects, at least a portion of the second bottoms stream is recycled. In some of these aspects, the recycled stream comprises from 0 wt. % to 40 wt. % heavies.

According to another embodiment, the present disclosure relates to a process for purifying TCH, the process comprising: a first separating step of flashing an adiponitrile process stream to form a first overhead stream comprising low-boiling components and high-boiling components, and a first bottoms stream comprising high-boiling components; a second separating step of distilling the first overhead stream to form a second overhead stream comprising low-boiling components, and a second bottoms stream comprising TCH and heavies; a third separating step of distilling the second bottoms stream to form a third distillate comprising TCH and impurities, and a third bottoms stream comprising heavies; and a fourth separating step of distilling the third distillate to form a fourth overhead stream comprising low-boiling components, and a fourth bottoms stream comprising TCH and less than 5 wt. % impurities wherein the residence time in the second, third, or fourth separating step is less than 8 hours. In some aspects, the fourth overhead stream comprises low-boiling components formed by the decomposition of high-boiling components during the second separating step. In some aspects, at least a portion of the second, third, or fourth bottoms stream is recycled. In some of these aspects, the recycled stream comprises from 0 wt % to 40 wt % heavies.

According to another embodiment, the present disclosure relates to a process for purifying TCH, the process comprising: a first separating step of separating an adiponitrile process stream to form a first overhead stream comprising low-boiling components and high-boiling components, and a first bottoms stream comprising high-boiling components; a second separating step of distilling the first overhead stream to form a second overhead stream comprising low-boiling components, and a second bottoms stream comprising TCH and heavies; third separating step of distilling the second bottoms stream to form a third distillate comprising TCH and impurities, and a third bottoms stream comprising heavies; and a fourth separating step of flashing the third distillate in a second flash vessel to form a fourth overhead stream comprising low-boiling components, and a fourth bottoms stream comprising TCH and less than 5 wt. % impurities wherein the residence time in the second or third separating step is less than 8 hours. In some aspects, the fourth overhead stream comprises low-boiling components formed by the decomposition of high-boiling components during the second and/or third separating step. In some aspects, at least a portion of the second or third bottoms stream is recycled. In some of these aspects, the recycled stream comprises from 0 wt. % to 40 wt. % heavies.

BRIEF DESCRIPTION OF THE DRAWINGS

The disclosure is described in detail below with reference to the appended drawings, wherein like numerals designate similar parts.

DETAILED DESCRIPTION

Introduction

As noted above, some conventional production processes co-product streams, e.g., adiponitrile production process co-product streams, contain amounts of desirable by-products, e.g., tricyanohexane (TCH) (sometimes referred to as 1,3,6-hexane-tricarbonitrile and/or 1,2,6-hexane-tricarbonitrile). Typically these streams are treated as waste streams, e.g., burned. However, the inventors have found that repurposing the streams would be preferable in light of the co-product and/or by-products present therein. In particular, because TCH is valuable, there is a desire to recover it to yield a (saleable) TCH product.

Some TCH-containing co-product streams contain a number of low-boiling and high-boiling impurities in addition to the TCH. Although conventional methods of separating impurities on the basis of differing boiling points are known, the inventors have found such methods to be unsuccessful in effectively separating TCH from the co-product streams. In particular, it has been discovered that certain high-boiling impurities are prone to decomposition into other impurities, including those with lower or higher boiling points, during conventional separation processes. The decomposition products may have been found to limit the capability of meeting commercially desirable purity of TCH. Conventional TCH recovery processes do not account for this decomposition and, as a result, require additional purification steps, causing lower efficiencies. In particular, the inventors have found that the residence time of the feed streams in the various purification operations affects the decomposition, and that by limiting residence time, e.g., to less than 8 hours in a particular purification operation, optionally at particular temperatures, significant improvements in purification are achieved.

The inventors have also found that the concentration of certain (non-TCH) components of streams of the purification processes may affect the purity of the resulting TCH product. For example, the inventors have now discovered that a higher concentration of high-boiling components in a bottoms stream or streams of the purification process (which may optionally be recycled upstream) unexpectedly contributes to higher purity TCH product. Conventional methods of separation and/or purification of TCH provide little or no guidance relating to the effect of these component concentrations on the final TCH yield. Importantly, the inventors have found that these high-boiling component concentrations can be effectively manipulated to provide significant efficiency improvements, which result in a higher purity TCH product.

The present disclosure relates to a process for purifying TCH present in a feed stream, e.g., an adiponitrile process stream. The process comprises a (first) separating step of separating the adiponitrile process stream to form a first overhead stream and a first bottoms stream. The first overhead stream comprises low-boiling components (lights) and high-boiling components (heavies), and the first bottoms stream comprises high-boiling components. The process further comprises a (second) separating step of separating the first overhead stream, optionally in one or more distillation columns, to form a lights stream comprising low-boiling components, a heavies stream comprising high-boiling components, and a TCH stream comprising TCH and less than 5 wt. % of impurities. Importantly, the residence time of feed streams in the individual operations of the process is minimized, e.g., less than 8 hours. In doing so, decomposition of high-boiling components is advantageously reduced or minimized, which provides for the separation efficiencies mentioned above.

Feed Stream

The process of the present disclosure may begin with a specific feed stream containing TCH and impurities. In particular, the feed stream may comprise TCH, high-boiling components, and low boiling components. In some embodiments, the feed stream may be one or more co-product streams of another industrial chemical production process. For example, the feed stream may comprise one or more co-product streams from different processes or systems, e.g., the production of adiponitrile, acrylonitrile, allyl cyanide, butyronitrile, polyacrylonitrile, polyamides, polyaramids, or combinations thereof. In a specific case, the feed stream may be an adiponitrile process stream, e.g., one or more co-product streams, purge streams, or flash tails from an adiponitrile production process. In some cases, co-product streams from multiple processes for may be combined to form the feedstock stream. In conventional process, such TCH-containing co-product streams are often treated as waste streams, e.g., vented or burned, and the valuable TCH components are not recovered. In some conventional TCH recovery processes, these co-product streams may be partially purified using multiple wiped film evaporators, but such processes require multiple rounds of purification to achieve commercially adequate levels of TCH purity and have relatively low yields. By recovering TCH from these streams, as described herein, the TCH may be recovered and used or sold, thus increasing efficiency and profitability.

The feed stream, e.g., the adiponitrile process stream, comprises TCH. In some embodiments, the feed stream comprises a relatively low content of TCH. In one embodiment, the feed stream comprises TCH in an amount ranging from 0 wt. % to 90 wt. %, based on the total weight of the feed stream, e.g., from 0 wt. %, to 89 wt. %, from 0 wt. % to 88 wt. %, from 0 wt. % to 85 wt. %, from 0 wt. % to 84 wt. %, from 10 wt. % to 90 wt. %, from 10 wt. %, to 89 wt. %, from 10 wt. % to 88 wt. %, from 10 wt. % to 85 wt. %, from 10 wt. % to 84 wt. %, from 20 wt. % to 90 wt. %, from 20 wt. %, to 89 wt. %, from 20 wt. % to 88 wt. %, from 20 wt. % to 85 wt. %, from 20 wt. % to 84 wt. %, from 30 wt. % to 90 wt. %, from 30 wt. %, to 89 wt. %, from 30 wt. % to 88 wt. %, from 30 wt. % to 85 wt. %, from 30 wt. % to 84 wt. %, from 40 wt. % to 90 wt. %, from 40 wt. %, to 89 wt. %, from 40 wt. % to 88 wt. %, from 40 wt. % to 85 wt. %, from 40 wt. % to 84 wt. %, from 50 wt. % to 90 wt. %, from 50 wt. %, to 89 wt. %, from 50 wt. % to 88 wt. %, from 50 wt. % to 85 wt. %, or from 50 wt. % to 84 wt. %. In some embodiments, the feed stream may comprise from 60 wt. % to 90 wt. % TCH, e.g., from 65 wt. % to 90 wt. %, from 70 wt. % to 90 wt. %, from 75 wt. % to 90 wt. %, from 60 wt. % to 85 wt. %, from 65 wt. % to 85 wt. %, from 70 wt. % to 85 wt. %, from 75 wt. % to 85 wt. %, from 60 wt. % to 82 wt. %, from 65 wt. % to 82 wt. %, from 70 wt. % to 82 wt. %, or from 75 wt. % to 82 wt. %. In terms of upper limits, the feed stream may comprise less than 90 wt. % TCH, e.g., 89 wt. %., less than 88 wt. %, less than 85 wt. %, or less than 84 wt. %, In terms of lower limits, the feed stream may comprise greater than 0 wt. % TCH, e.g., greater than 10 wt. %, greater than 20 wt. %, greater than 30 wt. %, greater than 40 wt. %, greater than 50 wt. %, greater than 60 wt. %, greater than 65 wt. %, greater than 70 wt. %, or greater than 75 wt. %.

Generally, as used herein, the weight percentages are based on the total weight of the respective stream. With respect to the feed stream, the weight percentages include all components of the stream, including a significant portion of water. It is contemplated that a feed stream comprising less water, e.g., a partially dehydrated or fully dehydrated feed stream, may be employed. In such a case, the component percentages discussed herein could easily be recalculated/derived by starting with the aforementioned component percentages and recalculating based on a lesser amount of water, e.g., taking water out of the basis for the weight percent calculation.

The feed stream also comprises low-boiling components (lights). Generally, the low-boiling components are impurities having relatively low boiling points. For example, each of the low-boiling components may have a boiling point of less than 415° C., e.g., less than 410° C., less than 400° C., less than 395° C., or less than 390° C. Examples of low-boiling components that may be present in the feed stream include various cyanocarbons, e.g., acrylonitrile, propionitrile, hydroxypropionitrile, monocyanoethyl propylamine, succinonitrile, methylglutaronitrile, adiponitrile, 2-cyanocyclopentylidenimine, bis-2-cyanoethyl ether, di(2-cyanoethyl) amine, di-2-cyanoethyl propylamine, cyanovaleramide and combinations thereof.

In one embodiment, the feed stream comprises low-boiling components in an amount ranging from 0 wt. % to 70 wt. %, e.g., from 0 wt. %, to 65 wt. %, from 0 wt. % to 60 wt. %, from 0 wt. % to 55 wt. %, from 0 wt. % to 50 wt. %, from 5 wt. % to 70 wt. %, from 5 wt. %, to 65 wt. %, from 5 wt. % to 60 wt. %, from 5 wt. % to 55 wt. %, from 5 wt. % to 50 wt. %, from 10 wt. % to 70 wt. %, from 10 wt. %, to 65 wt. %, from 10 wt. % to 60 wt. %, from 10 wt. % to 55 wt. %, from 10 wt. % to 50 wt. %, from 12 wt. % to 70 wt. %, from 12 wt. %, to 65 wt. %, from 12 wt. % to 60 wt. %, from 12 wt. % to 55 wt. %, from 12 wt. % to 50 wt. %, from 15 wt. % to 70 wt. %, from 15 wt. %, to 65 wt. %, from 15 wt. % to 60 wt. %, from 15 wt. % to 55 wt. %, or from 15 wt. % to 50 wt. %. In some embodiments, the feed stream may comprise from 0 wt. % to 20 wt. % low-boiling components, e.g. from 0 wt. % to 15 wt. %, from 0 wt. % to 12 wt. %, from 0 wt. % to 10 wt. %, from 0 wt. % to 8 wt. %, from 2 wt. % to 20 wt. %, from 2 wt. % to 15 wt. %, from 2 wt. % to 12 wt. %, from 2 wt. % to 10 wt. %, from 2 wt. % to 8 wt. %, from 4 wt. % to 20 wt. %, from 4 wt. % to 15 wt. %, from 4 wt. % to 12 wt. %, from 4 wt. % to 10 wt. %, or from 4 wt. % to 8 wt. %. In terms of upper limits, the feed stream may comprise less than 70 wt. % low-boiling components, e.g., less than 65 wt. %, less than 60 wt. %, less than 55 wt. %, or less than 50 wt. %. In terms of lower limits, the feed stream may comprise greater than 0 wt. %, low-boiling components, e.g., greater than 5 wt. %, greater than 10 wt. %, greater than 12 wt. %, or greater than 15 wt. %.

The feed stream also comprises high-boiling components (heavies). Generally, the high-boiling components are impurities having relatively high boiling points. For example, each of the high-boiling components may have a boiling point of greater than 395° C., e.g., greater than 400° C., greater than 405° C., greater than 408° C., greater than 410° C., or greater than 415° C. Examples of high-boiling components that may be present in the feed stream include isomeric tricyanohexane, tri(2-cyanoethyl)amine, and combinations thereof.

In one embodiment, the feed stream comprises high-boiling components in an amount ranging from 0 wt. % to 50 wt. %, e.g., from 0 wt. % to 40 wt. %, from 0 wt. % to 35 wt. %, from 0 wt. % to 25 wt. %, from 0 wt. % to 20 wt. %, from 0.5 wt. % to 50 wt. %, from 0.5 wt. % to 40 wt. %, from 0.5 wt. % to 35 wt. %, from 0.5 wt. % to 25 wt. %, from 0.5 wt. % to 20 wt. %, from 1 wt. % to 50 wt. %, from 1 wt. % to 40 wt. %, from 1 wt. % to 35 wt. %, from 1 wt. % to 25 wt. %, from 1 wt. % to 20 wt. %, from 2 wt. % to 50 wt. %, from 2 wt. % to 40 wt. %, from 2 wt. % to 35 wt. %, from 2 wt. % to 25 wt. %, from 2 wt. % to 20 wt. %, from 3 wt. % to 50 wt. %, from 3 wt. % to 40 wt. %, from 3 wt. % to 35 wt. %, from 3 wt. % to 25 wt. %, from 3 wt. % to 20 wt. %, from 5 wt. % to 50 wt. %, from 5 wt. % to 40 wt. %, from 5 wt. % to 35 wt. %, from 5 wt. % to 25 wt. %, or from 5 wt. % to 20 wt. %. In some embodiments, the feed stream comprises from 3 wt. % to 25 wt. % high-boiling components, e.g. from 3 wt. % to 20 wt. %., from 3 wt. % to 15 wt. %, from 3 wt. % to 12 wt. %, from 5 wt. % to 25 wt. %, from 5 wt. % to 20 wt. %., from 5 wt. % to 15 wt. %, or from 5 wt. % to 12 wt. %. In terms of upper limits, the feed stream may comprise less than 50 wt. % high-boiling components, e.g., less than 40 wt. %, less than 35 wt. %, less than 30 wt. %, less than 25 wt. % or less than 20 wt. %. In terms of lower limits, the feed stream may comprise greater than 0 wt. %, e.g., greater than 0.5 wt. %, greater than 1 wt. %, greater than 2 wt. %, greater than 3 wt. %, or greater than 5 wt. %.

In some embodiments, the feed stream may also comprise solid impurities. These impurities may include various organic impurities that are solid under the temperature and pressure conditions. For example, the solid impurities may include solid cyanocarbon compounds. In one embodiment, the feed stream comprises solid impurities in an amount ranging from 0 wt. % to 25 wt. %, e.g., from 0 wt. % to 20 wt. %, from 0 wt. % to 15 wt. %, or from 0 wt. % to 10 wt. %. In terms of upper limits, the feed stream may comprise less than 25 wt. %, e.g., less than 20 wt. %, less than 15 wt. %, or less than 10 wt. %.

The feed stream may further comprise adiponitrile. In one embodiment, the feed stream comprises adiponitrile in an amount ranging from 0 wt. % to 15 wt. %, e.g., from 0 wt. % to 12 wt. %, from 0 wt. % to 10 wt. %, from 0 wt. % to 8 wt. %, from 0 wt. % to 5 wt. %, from 1 wt. % to 15 wt. %, from 1 wt. % to 12 wt. %, from 1 wt. % to 10 wt. %, from 1 wt. % to 8 wt. %, from 1 wt. % to 5 wt. %, from 2 wt. % to 15 wt. %, from 2 wt. % to 12 wt. %, from 2 wt. % to 10 wt. %, from 2 wt. % to 8 wt. %, from 2 wt. % to 5 wt. %, from 3 wt. % to 15 wt. %, from 3 wt. % to 12 wt. %, from 3 wt. % to 10 wt. %, from 3 wt. % to 8 wt. %, from 3 wt. % to 5 wt. %, from 4 wt. % to 15 wt. %, from 4 wt. % to 12 wt. %, from 4 wt. % to 10 wt. %, from 4 wt. % to 8 wt. %, or from 4 wt. % to 5 wt. %. In some embodiments, the feed stream may comprise from 0 wt. % to 15 wt. % adiponitrile, e.g., from 0 wt. % to 12 wt. %, from 0 wt. % to 10 wt. %, from 0 wt. % to 8 wt. %, from 2 wt. % to 15 wt. %, from 2 wt. % to 12 wt. %, from 2 wt. % to 10 wt. %, from 2 wt. % to 8 wt. %, from 4 wt. % to 15 wt. %, from 4 wt. % to 12 wt. %, from 4 wt. % to 10 wt. %, or from 4 wt. % to 8 wt. %. In terms of upper limits, the feed stream may comprise less than 15 wt. % adiponitrile, e.g., less than 12 wt. %, less than 10 wt. %, less than 8 wt. %, or less than 5 wt. %. In terms of lower limits, the feed stream may comprise greater than 0 wt. %, e.g., greater than 1 wt. %, greater than 2 wt. %, greater than 3 wt. %, or greater than 4 wt. %.

First Separating Step

As noted above, the feed stream, e.g., an adiponitrile process stream, is separated in a first separating step to form a first overhead stream comprising low-boiling components (lights) and (optionally lower amounts of) high-boiling components (heavies) and a first bottoms stream comprising high-boiling components and solid impurities. The first separating step, in some cases, removes a significant portion (if not all) of the heavies and/or the solid impurities present in the feed stream. The inventors have found that removal of the heavies prior to processing in the second separating step beneficially reduces the decomposition of the high-boiling components and thereby improves the efficiency of the total purification process. Without this initial removal of heavies, additional non-TCH impurities are formed, which must then be separated, creating additional operations and uncertainties. Furthermore, the inventors have also found that early removal of the heavies and the solid impurities reduces fouling of distillation columns, which improves downstream efficiency and eliminates or reduces the need for subsequent separation operations. The residence time of the feed stream in the first separation step may be a short residence time as discussed herein.

In some embodiments, the first separating step includes separation in a flasher, e.g., a flash evaporator. In these embodiments, the feed stream is evaporated and separated into the first overhead stream and the first bottoms stream. Various flashers are known to those of ordinary skill in the art, and any suitable flasher may be employed as long as the separation described herein is achieved. In some embodiments, the separation in the flasher may be caused by reducing the pressure, e.g., an adiabatic flash, without heating the feed stream. In other embodiments, the separation in the flasher may be caused by raising the temperature of the feed stream without changing the pressure. In still other embodiments, the separation in the flasher may be caused by reducing the pressure while heating the feed stream. In some embodiments, the first separating step is achieved via a wiped film evaporator (WFE).

In some embodiments, the first separating step includes separating the feed stream in a flash evaporator at reduced pressure, e.g., under a vacuum. In some embodiments, the pressure in the flash evaporator is reduced to less than 25 torr, e.g., less than 20 torr, less than 10 torr, or less than 5 torr.

In some embodiments, the flash vessel of the first separating step is kept at a constant temperature. In some embodiments, the temperature of the flash vessel may be from 175° C. to 235° C., e.g., from 180° C. to 230° C., from 185° C. to 225° C., or from 190° C. to 220° C.

The first bottoms stream comprises high-boiling components (heavies). Examples of heavies that may be present in the first bottoms stream include isomeric tricyanohexane, tri(2-cyanoethyl)amine, and combinations thereof. In one embodiment, the first separation step includes in a flasher, and the first bottoms stream comprises isomeric tricyanohexane and tri(2-cyanoethyl)amine.

The first bottoms stream also comprises solid impurities. In one embodiment, the first separation step removes all (i.e., 100%) of the solid impurities from the feed stream. Said another way, in this embodiment, the first overhead stream comprises 0 wt. % solid impurities. In other embodiments, the first separation step may remove less than 100% of the solid impurities, e.g., less than 99.9%, less than 99%, or less than 98%.

The first overhead stream comprises heavies and lights. The first overhead stream also comprises TCH. In some embodiments, the first overhead stream comprises TCH in a higher concentration than that of the feed stream. In one embodiment, the first overhead stream comprises TCH in an amount ranging from 60 wt. % to 98 wt. %, e.g., from 60 wt. % to 97 wt. %, from 60 wt. % to 96 wt. %, from 60 wt. % to 95 wt. %, from 65 wt. % to 98 wt. %, from 65 wt. % to 97 wt. %, from 65 wt. % to 96 wt. %, from 65 wt. % to 95 wt. %, from 70 wt. % to 98 wt. %, from 70 wt. % to 97 wt. %, from 70 wt. % to 96 wt. %, from 70 wt. % to 95 wt. %, from 75 wt. % to 98 wt. %, from 75 wt. % to 97 wt. %, from 75 wt. % to 96 wt. %, or from 75 wt. % to 95 wt. %. In terms of upper limits, the first overhead stream may comprise less than 98 wt. % TCH, e.g., less than 97 wt. %, less than 96 wt. %, or less than 95 wt. %. In terms of lower limits, the first overhead stream may comprise greater than 60 wt. % TCH, e.g., greater than 65 wt. %, greater than 70 wt. %., or greater than 75 wt. %.

In one embodiment, the first overhead stream comprises lights in an amount ranging from 0 wt. % to 30 wt. %, e.g., from 0 wt. % to 25 wt. %, from 0 wt. %, to 20 wt. %, from 0 wt. % to 15 wt. %, from 0 wt. % to 10 wt. %, from 1 wt. % to 30 wt. %, from 1 wt. % to 25 wt. %, from 1 wt. %, to 20 wt. %, from 1 wt. % to 15 wt. %, from 1 wt. % to 10 wt. %, from 2 wt. % to 30 wt. %, from 2 wt. % to 25 wt. %, from 2 wt. %, to 20 wt. %, from 2 wt. % to 15 wt. %, from 2 wt. % to 10 wt. %, from 3 wt. % to 30 wt. %, from 3 wt. % to 25 wt. %, from 3 wt. %, to 20 wt. %, from 3 wt. % to 15 wt. %, from 3 wt. % to 10 wt. %, from 4 wt. % to 30 wt. %, from 4 wt. % to 25 wt. %, from 4 wt. %, to 20 wt. %, from 4 wt. % to 15 wt. %, from 4 wt. % to 10 wt. %, from 5 wt. % to 30 wt. %, from 5 wt. % to 25 wt. %, from 5 wt. %, to 20 wt. %, from 5 wt. % to 15 wt. %, or from 5 wt. % to 10 wt. %. In terms of upper limits, the first overhead stream may comprise less than 30 wt. % lights, e.g., less than 25 wt. %, less than 20 wt. %, less than 15 wt. %, or less than 10 wt. %. In terms of lower limits, the first overhead stream may comprise greater than 0 wt. % lights, e.g., greater than 1 wt. %, greater than 2 wt. %, greater than 3 wt. %, greater than 4 wt. %, or greater than 5 wt. %.

In one embodiment, the first overhead stream comprises heavies in an amount ranging from 0 wt. % to 20 wt. %, e.g., from 0 wt. % to 15 wt. %, from 0 wt. % to 10 wt. %, from 0 wt. % to 8 wt. %, from 0 wt. % to 5 wt. %, from 0.5 wt. % to 20 wt. %, from 0.5 wt. % to 15 wt. %, from 0.5 wt. % to 10 wt. %, from 0.5 wt. % to 8 wt. %, from 0.5 wt. % to 5 wt. %, from 1 wt. % to 20 wt. %, from 1 wt. % to 15 wt. %, from 1 wt. % to 10 wt. %, from 1 wt. % to 8 wt. %, from 1 wt. % to 5 wt. %, from 1.5 wt. % to 20 wt. %, from 1.5 wt. % to 15 wt. %, from 1.5 wt. % to 10 wt. %, from 1.5 wt. % to 8 wt. %, from 1.5 wt. % to 5 wt. %, from 2 wt. % to 20 wt. %, from 2 wt. % to 15 wt. %, from 2 wt. % to 10 wt. %, from 2 wt. % to 8 wt. %, from 2 wt. % to 5 wt. %, from 2.5 wt. % to 20 wt. %, from 2.5 wt. % to 15 wt. %, from 2.5 wt. % to 10 wt. %, from 2.5 wt. % to 8 wt. %, or from 2.5 wt. % to 5 wt. %. In terms of upper limits, the first overhead stream may comprise less than 20 wt. % heavies, e.g., less than 15 wt. %, less than 10 wt. %, less than 8 wt. %, or less than 5 wt. %. In terms of lower limits, the first overhead stream may comprise greater than 0 wt. % heavies, e.g., greater than 0.5 wt. %, greater than 1 wt. %, greater than 1.5 wt. %, greater than 2 wt. %, or greater than 2.5 wt. %.

In some cases, the first separation step removes a significant portion of the heavies from the feed stream. Said another, the first overhead stream comprises low amounts, if any, of the heavies initially present in the feed stream. In some embodiments, the first overhead stream comprises less than 70% of the heavies present in the feed stream, e.g., less than 65%, less than 60%, less than 55%, or less than 50%.

Second Separating Step

As noted above, the first overhead stream is subjected to further purification in the second separating step. In particular, the first overhead stream is separated in a second separation step to form a lights stream comprising lights (low-boiling components), a heavies stream comprising heavies (high-boiling components), and a TCH stream comprising TCH. The first separating step, in some cases, removes a significant portion (if not all) of the low-boiling components and high-boiling components present in the first overhead stream. The residence time of the feed stream in the second separation step may be a short residence time as discussed herein.

The lights stream comprises lights, e.g., the above-described impurities having relatively low boiling points. In one embodiment, the lights stream comprises low-boiling components in an amount ranging from 10 wt. % to 60 wt. %, e.g., from 10 wt. % to 55 wt. %, from 10 wt. % to 45 wt. %, from 10 wt. % to 40 wt. %, from 10 wt. % to 35 wt. %, from 15 wt. %, to 60 wt. %, from 15 wt. % to 55 wt. %, from 15 wt. % to 45 wt. %, from 15 wt. % to 40 wt. %, from 15 wt. % to 35 wt. %, from 20 wt. %, to 60 wt. %, from 20 wt. % to 55 wt. %, from 20 wt. % to 45 wt. %, from 20 wt. % to 40 wt. %, from 20 wt. % to 35 wt. %, from 25 wt. %, to 60 wt. %, from 25 wt. % to 55 wt. %, from 25 wt. % to 45 wt. %, from 25 wt. % to 40 wt. %, from 25 wt. % to 35 wt. %, from 30 wt. %, to 60 wt. %, from 30 wt. % to 55 wt. %, from 30 wt. % to 45 wt. %, from 30 wt. % to 40 wt. %, or from 30 wt. % to 35 wt. %. In some embodiments, the light stream comprises from 10 wt. % to 30 wt. % low-boiling components, e.g., from 10 wt. % to 25 wt. %, from 10 wt. % to 20 wt. %, or from 10 wt. % to 15 wt. %. In terms of upper limits, the lights stream may comprise less than 60 wt. % low-boiling components, e.g., less than 55 wt. %, less than 45 wt. %, less than 40 wt. %, or less than 35 wt. %. In terms of lower limits, the lights stream may comprise greater than 10 wt. % low-boiling components, e.g., greater than 15 wt. %, greater than 20 wt. %, greater than 25 wt. %, or greater than 30 wt. %.

The heavies stream comprises high-boiling components (heavies). In one embodiment, the heavies stream comprises high-boiling components in an amount ranging from 5 wt. % to 50 wt. %, e.g., from 5 wt. % to 45 wt. %, from 5 wt. % to 40 wt. %, from 5 wt. % to 35 wt. %, from 5 wt. % to 30 wt. %, from 8 wt. % to 50 wt. %, from 8 wt. % to 45 wt. %, from 8 wt. % to 40 wt. %, from 8 wt. % to 35 wt. %, from 8 wt. % to 30 wt. %, from 10 wt. % to 50 wt. %, from 10 wt. % to 45 wt. %, from 10 wt. % to 40 wt. %, from 10 wt. % to 35 wt. %, from 10 wt. % to 30 wt. %, from 12 wt. % to 50 wt. %, from 12 wt. % to 45 wt. %, from 12 wt. % to 40 wt. %, from 12 wt. % to 35 wt. %, from 12 wt. % to 30 wt. %, from 15 wt. % to 50 wt. %, from 15 wt. % to 45 wt. %, from 15 wt. % to 40 wt. %, from 15 wt. % to 35 wt. %, or from 15 wt. % to 30 wt. %. In some embodiments, the heave stream comprises from 5 wt. % to 30 wt. % high-boiling components, e.g. from 5 wt. % to 25 wt. %, from 5 wt. % to 20 wt. %, or from 5 wt. % to 15 wt. %. In terms of upper limits, the heavies stream may comprise less than 50 wt. % high-boiling components, e.g., less than 45 wt. %, less than 40 wt. %, less than 35 wt. %, or less than 30 wt. %. In terms of lower limits, the heavies stream may comprise greater than 5 wt. % high-boiling components, e.g., greater than 8 wt. %, greater than 10 wt. %, greater than 12 wt. %, or greater than 15 wt. %.

The TCH stream comprises TCH. In one embodiment, the TCH stream comprises TCH in an amount ranging from 90 wt. % to 100 wt. %, e.g., from 90 wt. % to 99.9 wt. %, from 90 wt. % to 99 wt. %, from 90 wt. % to 98 wt. %, from 92.5 wt. % to 100 wt. %, from 92.5 wt. % to 99.9 wt. %, from 92.5 wt. % to 99 wt. %, from 92.5 to 98 wt. %, from 95 wt. % to 100 wt. %, from 95 wt. % to 99.9 wt. %, from 95 wt. % to 99 wt. %, from 95 to 98 wt. %, from 97.5 wt. % to 100 wt. %, from 97.5 wt. % to 99.9 wt. %, from 97.5 to 99 wt. %, or 97.5 to 98 wt. %. In terms of upper limits, the TCH stream may comprise less than 100 wt. % TCH, e.g., less than 99.9 wt. % less than 99 wt. %, or less than 98 wt. %. In terms of lower limits, the TCH stream may comprise greater than 90 wt. %, e.g., greater than 92.5 wt. %, greater than 95 wt. %, or greater than 97.5 wt. %. Conventional processes have been unable to achieve such high TCH purity levels.

The TCH purification methods disclosed herein produce a high-purity TCH stream. Nevertheless, the TCH stream may still comprise some impurities. Generally, these impurities are present in relatively small amounts. Impurities present in the TCH stream are typically nitrile compounds and may have amide and/or oxime functionalities. Examples of impurities that may be present in the TCH stream include adiponitrile, di(2-cyanoethyl) amine, di(2-cyanoethyl) propylamine, tri(2-cyanoethyl) amine, cyanovaleramide, and combinations thereof. The TCH stream may also comprise small amounts of other high-boiling and/or low-boiling impurities. Unlike various other impurities that present in lower-purity, conventional TCH products, these impurities are typically nitrile compounds. As such, they may improve the ultimate performance of the TCH product. Furthermore, the presence of impurities in the TCH stream may provide a fingerprint for the disclosed purification methods, e.g., a means of identifying a TCH product formed by an embodiment of the present disclosure.

In one embodiment, the TCH stream comprises impurities in an amount ranging from 0 wt. % to 10 wt. %, e.g., from 0 wt. % to 7.5 wt. %, from 0 wt. % to 5 wt. %, from 0 wt. % to 2.5 wt. %, from 0.1 wt. % to 10 wt. %, from 0.1 wt. % to 7.5 wt. %, from 0.1 wt. % to 5 wt. %, from 0.1 wt. % to 2.5 wt. %, from 1 wt. % to 10 wt. %, from 1 wt. % to 7.5 wt. %, from 1 wt. % to 5 wt. %, from 1 wt. % to 2.5 wt. %, from 2 wt. % to 10 wt. %, from 2 wt. % to 7.5 wt. %, from 2 wt. % to 5 wt. %, or from 2 wt. % to 2.5 wt. %. In some embodiments, the TCH stream comprises from 0 wt. % to 2.5 wt. % impurities, e.g., from 0 wt. % to 2 wt. %, from 0 wt. % to 1.5 wt. %, from 0 wt. % to 1 wt. %, from 0.5 wt. % to 2.5 wt. %, from 0.5 wt. % to 2 wt. %, from 0 wt. % to 1.5 wt. %, or from 0 wt. % to 1 wt. %. In terms of upper limits, the TCH stream may comprise less than 10 wt. % impurities, e.g., less than 7.5 wt. %, less than 5 wt. %, or less than 2.5 wt. %. In terms of lower limits, the TCH stream may comprise greater than 0 wt. % impurities, e.g., greater than 0.1 wt. %, greater than 1 wt. %, or greater than 2 wt. %.

In one embodiment, the TCH stream comprises from 0 wt. % to 0.05 wt. % adiponitrile, from 0 wt. % to 0.1 wt. % di(2-cyanoethyl) amine, from 0 wt. % to 0.05 wt. % cyanovaleramide, and from 0 wt. % to 0.05 wt. % tri(2-cyanoethyl) amine. In one embodiment, the TCH stream comprises from 0 wt. % to 0.01 wt. % adiponitrile, from 0 wt. % to 0.01 wt. % low-boiling components, and from 0 wt. % to 1 wt. % high-boiling components.

The second separating step may include separation of the first overheard stream in one or more distillation columns and/or in one or more flash evaporators. The structure of the one or more distillation columns may vary widely. Various distillation columns are known to those of ordinary skill in the art, and any suitable column may be employed in the second separation step as long as the separation described herein is achieved. For example, the distillation column may comprise any suitable separation device or combination of separation devices. For example, the distillation column may comprise a column, e.g., a standard distillation column, an extractive distillation column and/or an azeotropic distillation column. Similarly, as noted above, various flashers are known to those of ordinary skill in the art, and any suitable flasher may be employed in the second separation step as long as the separation described herein is achieved. For example, the flasher may comprise an adiabatic flash evaporator, a heated flash evaporator, or a wipe film evaporator, or combinations thereof.

Embodiments of the second separating step may include any combination of one or more distillation columns and/or one or more flashers, and a person of skill in the art would appreciate and understand how to combine these separators to achieve a separation that forms a lights stream, a heavies stream, and a TCH stream.

In some embodiments, the second separating step includes separation of the first overhead stream in two distillation columns. For example, the first overhead stream may be distilled in a first distillation column to form a second overhead stream, a second bottoms stream, and/or a side draw. The second bottoms stream and/or the side draw may then be distilled in a second distillation column to produce the TCH stream.

In some embodiments, the second separating step includes separation of the first overhead stream in three distillation columns. For example, the first overhead stream may be distilled in a first distillation column to form a second overhead stream, a second bottoms stream, and/or a side draw. The second bottoms stream and/or the side draw may then be distilled in a second distillation column to produce a third overhead stream and a third bottoms stream. The third overhead stream may then be distilled in a third distillation column to produce the TCH stream.

Decomposition

As noted above, the inventors now have found that, in conventional TCH purification processes, certain high-boiling components are prone to decomposition into impurities having both higher boiling points lower boiling points. The inventors have also found that even TCH can decompose at high temperatures in conventional processes. In particular, the inventors have now found that prolonged exposure to high temperatures and/or high pressure, such as in distillation columns, contributes to the decomposition of high-boiling components. By utilizing specific process parameters, this decomposition can be effectively mitigated.

In one aspect, the purification process may inhibit decomposition by reducing the residence time during which process streams are exposed to high temperatures, e.g., in a separation operation. Generally, process streams may be exposed to high temperatures in a distillation column. In order to reduce prolonged exposure to high temperatures, the process may reduce the residence time of a stream in a given column. For example, the process may control the residence time of the first overhead stream in a distillation column. In one embodiment, the process limits the residence time of a process stream in a distillation column to less than 8 hours, e.g., less than 7 hours, less than 6 hours, less than 5 hours, or less than 4 hours.

In one aspect, the purification processes may inhibit decomposition by reducing the exposure of process streams to high temperatures. For example, the process may control the temperature to which the first overhead stream is exposed, e.g., in a separation step. In one embodiment, the purification process limits the temperature at which separation step(s) are conducted. For example, operation temperature may be limited to less than 350° C., e.g., less than 325° C., less than 300° C., less than 275° C., or less than 250° C., In terms of ranges operation temperature may range from 225° C. to 350° C., e.g., from 250° C. to 325° C. or from 275° C. to 300° C., or from 250° C. to 275° C.

In some aspects, the process may control both the temperature to which a stream is exposed and the time for which it is exposed to that temperature. For example, the process may control the residence time of the first overhead stream in a distillation column as well as the temperature of that distillation column. In one embodiment, the residence time of a stream in temperatures above 230° C. is less than 8 hours. The aforementioned ranges and limits for temperature and residence time may be combined with one another.

In some aspects, the purification processes may inhibit decomposition by reducing the exposure of process streams to high pressures. For example, the process may control the pressure to which the first overhead stream is exposed, e.g., in a separation step. In one embodiment, the purification process limits the pressure at which separation step(s) are conducted. For example, operation pressure may be limited to less than 50 torr, e.g., less than 45 torr, less than 40 torr, less than 35 torr, less than 30 torr, or less than 25 torr. In order to reduce prolonged exposure to high pressures, the process may reduce the residence time of a stream in a given column. For example, the process may control the residence time of the first overhead stream in a high-pressure distillation column (e.g., a column with a pressure greater than 50 torr). In one embodiment, the process limits the residence time of a process stream in a distillation column to less than 8 hours, e.g., less than 7 hours, less than 6 hours, less than 5 hours, or less than 4 hours.

In some aspects, the process may control both the temperature to which a stream is exposed and the pressure to which it is exposed. In one embodiment, the process may be controlled such that the stream is not exposed to temperatures above 300° C. or pressures above 35 torr.

In other aspects, the purification process may inhibit decomposition by utilizing distillation columns with certain physical features. In particular, the distillation columns employed in the purification process may have certain shapes. In some embodiments, the distillation columns have relatively small sumps to minimize exposure to high temperatures. In these embodiments, the sumps of each column may taper to a smaller diameter, which allows or reduced exposure to higher temperatures.

These modifications to conventional purification processes reduce the decomposition of high-boiling components. In some embodiments, these modifications reduce the amount high-boiling components in the first overhead stream that decompose during the second separating step. In one embodiment, the amount of high-boiling components in the first overhead stream that decompose is less than 50 wt. % of the high-boiling components in the stream, e.g., less than 45 wt. %, less than 40 wt. %, or less than 30 wt. %. In terms of lower limits, the amount of high-boiling components that decompose may be greater than 0 wt. % of the high-boiling components in the stream, e.g., greater than 5 wt. %, greater than 10 wt. %, or greater than 15 wt. %. In terms of ranges, the amount of high-boiling components that decompose may be from 0 wt. %. to 50 wt. %, e.g., from 0 wt. % to 45 wt. %, from 0 wt. % to 40 wt. %, from 0 wt. % to 30 wt. %, from 5 wt. % to 50 wt. %, from 5 wt. % to 45 wt. %, from 5 wt. % to 40 wt. %, from 5 wt. % to 30 wt. %, from 10 wt. % to 50 wt. %, from 10 wt. % to 45 wt. %, from 10 wt. % to 40 wt. %, from 10 wt. % to 30 wt. %, from 15 wt. % to 50 wt. %, from 15 wt. % to 45 wt. %, from 15 wt. % to 40 wt. %, or from 15 wt. % to 30 wt. %.

As noted above, the high-boiling components may decompose into other high-boiling impurities and/or into low-boiling impurities. In some cases, the high-boiling components may decompose into other high-boiling impurities that were not otherwise present in the system. Said another way, the decomposition may cause the total number of high-boiling impurity compounds in the system to increase. By inhibiting decomposition, as described herein, the increase in the total number of high-boiling impurity compounds present in the system, caused by decomposition, may be reduced.

Recycle Step

As noted above, the inventors have now found that the concentration of certain components of streams in the TCH purification process affects the ultimate purity of the TCH product. For example, the inventors have now found that a higher concentration of high-boiling components in a bottoms stream or streams of the purification process correlates with higher purity TCH product. In particular, the present inventors have found that higher concentrations of high-boiling components (e.g., heavies) in a bottom stream of a distillation column (e.g., a distillation column of the second separating step) improves the separation efficiency of that column. This surprising and unexpected discovery can be incorporated into the TCH purification processes disclosed herein by recycling certain streams.

In some embodiments, for example, the separation efficiency of a given distillation column can be controlled (e.g., increased) by recycling the bottom stream produced by that distillation column. Because the bottom stream comprises a greater proportion of high-boiling components (e.g., heavies), recycling the bottom stream increases the concentration of high-boiling components in the stream fed to the distillation column. This further increases the content of high-boiling components in the bottom stream. In this way, a higher concentration of high-boiling components in the bottom stream of the distillation column can be achieved, and the separation efficiency of the distillation can be improved.

In some embodiments, the process comprises a recycle step of recycling at least a portion of a stream formed during the separation steps to a point upstream (target). For example, the recycling step may comprise recycling at least a portion of the heavies stream of one of the columns or flashers to a point upstream in the process. In some embodiments, the recycling step comprises recycling at least a portion of the second bottoms stream of the second separation step to the first overhead stream of the first separation step. In some embodiments, the recycling step comprises recycling at least a portion of the third bottoms stream to the first overhead stream of the first separation step and/or the second bottoms stream of the second separation step. In some embodiments, the recycling step comprises recycling at least a portion of the third bottoms stream to a side draw of the second separating step. Some of these embodiments are illustrated in FIGS. 1-5.

In one embodiment, the recycled stream comprises heavies, and the concentration of these heavies surprisingly affects the purity of the resultant TCH stream.

In some cases, the recycled stream comprises heavies in an amount ranging from 0 wt. % to 40 wt. %, e.g., from 0 wt. % to 37.5 wt. %, from 0 wt. % to 35 wt. %, from 0 wt. % to 32.5 wt. %, from 0 wt. % to 30 wt. %, from 5 wt. % to 40 wt. %, from 5 wt. % to 37.5 wt. %, from 5 wt. % to 35 wt. %, from 5 wt. % to 32.5 wt. %, from 5 wt. % to 30 wt. %, from 10 wt. % to 40 wt. %, from 10 wt. % to 37.5 wt. %, from 10 wt. % to 35 wt. %, from 10 wt. % to 32.5 wt. %, from 10 wt. % to 30 wt. %, from 15 wt. % to 40 wt. %, from 15 wt. % to 37.5 wt. %, from 15 wt. % to 35 wt. %, from 15 wt. % to 32.5 wt. %, from 15 wt. % to 30 wt. %, from 20 wt. % to 40 wt. %, from 20 wt. % to 37.5 wt. %, from 20 wt. % to 35 wt. %, from 20 wt. % to 32.5 wt. %, or from 20 wt. % to 30 wt. %. In some embodiments, the recycled stream comprises heavies in an amount from 0 wt. % to 30 wt. %, e.g., from 1 wt. % to 28 wt. %, from 2 wt. % to 26 wt. %, from 3 wt. % to 24 wt. %, from 4 wt. % to 22 wt. %, or from 5 wt. % to 20 wt. %. In terms of upper limits, the recycled stream may comprise less than 40 wt. % high-boiling components, e.g., less than 37.5 wt. %, less than 35 wt. %, less than 32.5 wt. %, or less than 30 wt. %. In terms of lower limits, the recycled stream may comprise greater than 0 wt. % high-boiling components, e.g., greater than 5 wt. %, greater than 10 wt. %, greater than 15 wt. %, or greater than 20 wt. %.

In some aspects, the recycle step controls the concentration of heavies in the target. For example, the recycle step may control the concentration of the heavies in the first overhead stream by recycling a stream containing heavies to the first overhead stream.

In one embodiment, due to the recycling, the recycle step controls the concentration of heavies in the target to be from 0 wt. % to 10 wt. %, e.g., from 0 wt. % to 9 wt. %, from 0 wt. % to 8 wt. %, from 0 wt. % to 7 wt. %, from 1 wt. % to 10 wt. %, from 1 wt. % to 9 wt. %, from 1 wt. % to 8 wt. %, from 1 wt. % to 7 wt. %, from 2 wt. % to 10 wt. %, from 2 wt. % to 9 wt. %, from 2 wt. % to 8 wt. %, from 2 wt. % to 7 wt. %, from 3 wt. % to 10 wt. %, from 3 wt. % to 9 wt. %, from 3 wt. % to 8 wt. %, or from 3 wt. % to 7 wt. %. In terms of upper limits, the recycle step may control the concentration of heavies in the target to be less than 10 wt. %, e.g., less than 9 wt. %, less than 8 wt. %, or less than 7 wt. %. In terms of lower limits, the recycle step may control the concentration of heavies in the target to be greater than 0 wt. %, e.g., greater than 1 wt. %, greater than 2 wt. %, or greater than 3 wt. %.

Treating Step

As noted above, the TCH stream produced in the second separating step may comprise impurities. These impurities may be removed by further purification methods. In some embodiments, the purification process further comprises a treating step of treating the TCH stream to form a purified TCH stream.

In some embodiments, the treating step may comprise nitrogen stripping. In some embodiments, the treating step may comprise treating with one or more types of molecular sieve. In some embodiments, the treating step may comprise a combination of treating with nitrogen stripping and treating with molecular sieves.

The purified TCH comprises a higher concentration of TCH than that of the TCH stream. In one embodiment, the purified TCH stream comprises TCH in an amount ranging from 95 wt. % to 100 wt. %, e.g., from 95 wt. % to 99.99 wt. %, from 95 wt. % to 99.9 wt. %, from 95 wt. % to 99 wt. %, from 96 wt. % to 100 wt. %, from 96 wt. % to 99.99 wt. %, from 96 wt. % to 99.9 wt. %, from 96 to 99 wt. %, from 97 wt. % to 100 wt. %, from 97 wt. % to 99.99 wt. %, from 97 wt. % to 99.9 wt. %, from 97 to 99 wt. %, from 98 wt. % to 100 wt. %, from 98 wt. % to 99.99 wt. %, from 98 to 99.9 wt. %, or from 98 to 99 wt. %. In terms of upper limits, the purified TCH stream may comprise less than 100 wt. % TCH, e.g., less than 99.99 wt. % less than 99.9 wt. %, or less than 99 wt. %. In terms of lower limits, the purified TCH stream may comprise greater than 95 wt. %, e.g., greater than 96 wt. %, greater than 97 wt. %, or greater than 98 wt. %.

The purified TCH stream comprises a lower concentration of impurities than that of the TCH stream. In some embodiments, the purified TCH stream comprises less than 2 wt. % impurities, e.g., less than 1.8 wt. %, less than 1.6 wt. %, less than 1.4 wt. %, less than 1.2 wt. %, or less than 1.0 wt. %. In one embodiment, the purified TCH stream comprises less than 0.1 wt. %, impurities, e.g., less than 0.09 wt. %, less than 0.05 wt. %, or less than 0.01 wt. %. For example, the purified TCH stream may comprise water as an impurity. In some embodiments, the purified TCH stream comprises less than 200 ppm water, e.g., less than 195 ppm, less than 190 ppm, less than 185 ppm, or less than 180 ppm. In one embodiment, the purified TCH stream comprises less than 20 ppm water, e.g., less than 15 ppm, less than 10 ppm, or less than 1 ppm. The purified TCH stream may comprise metals as impurities. In one embodiment, the purified TCH stream comprises less than 5 ppm metals, e.g., less than 4 ppm, less than 3 ppm, or less than 2 ppm.

Industrial Applications

The TCH purification processes disclosed herein are useful in purifying any process stream that comprises TCH and other impurities. In some embodiments, the TCH purification processes are a feature of other industrial production and purification processes. For example, the TCH purification processes may be used to purify TCH formed during the industrial production of adiponitrile or other cyanocarbons. In some embodiments, the feed stream is a process stream from adiponitrile production or purification, e.g., a co-product stream produced by an adiponitrile production and/or an adiponitrile purification process.

In conventional TCH purification methods, process streams formed during purification are considered waste streams and are otherwise discarded. In some embodiments of the present disclosure, however, process streams formed during the TCH purification processes disclosed herein may be recycled to other industrial processes, e.g., adiponitrile production and/or adiponitrile purification processes. This improves the overall efficiencies of the processes. In some embodiments, a portion of the first bottoms streams may be recycled to other industrial processes. In some embodiments, a portion of the lights stream may be recycled to other industrial processes. In one embodiment, a portion of both the first bottoms stream and the lights stream is recycled to an adiponitrile production and/or adiponitrile purification process.

Configurations

FIGS. 1-5 show schematic overviews of several configurations of the TCH purification processes disclosed herein.

Figure 1:
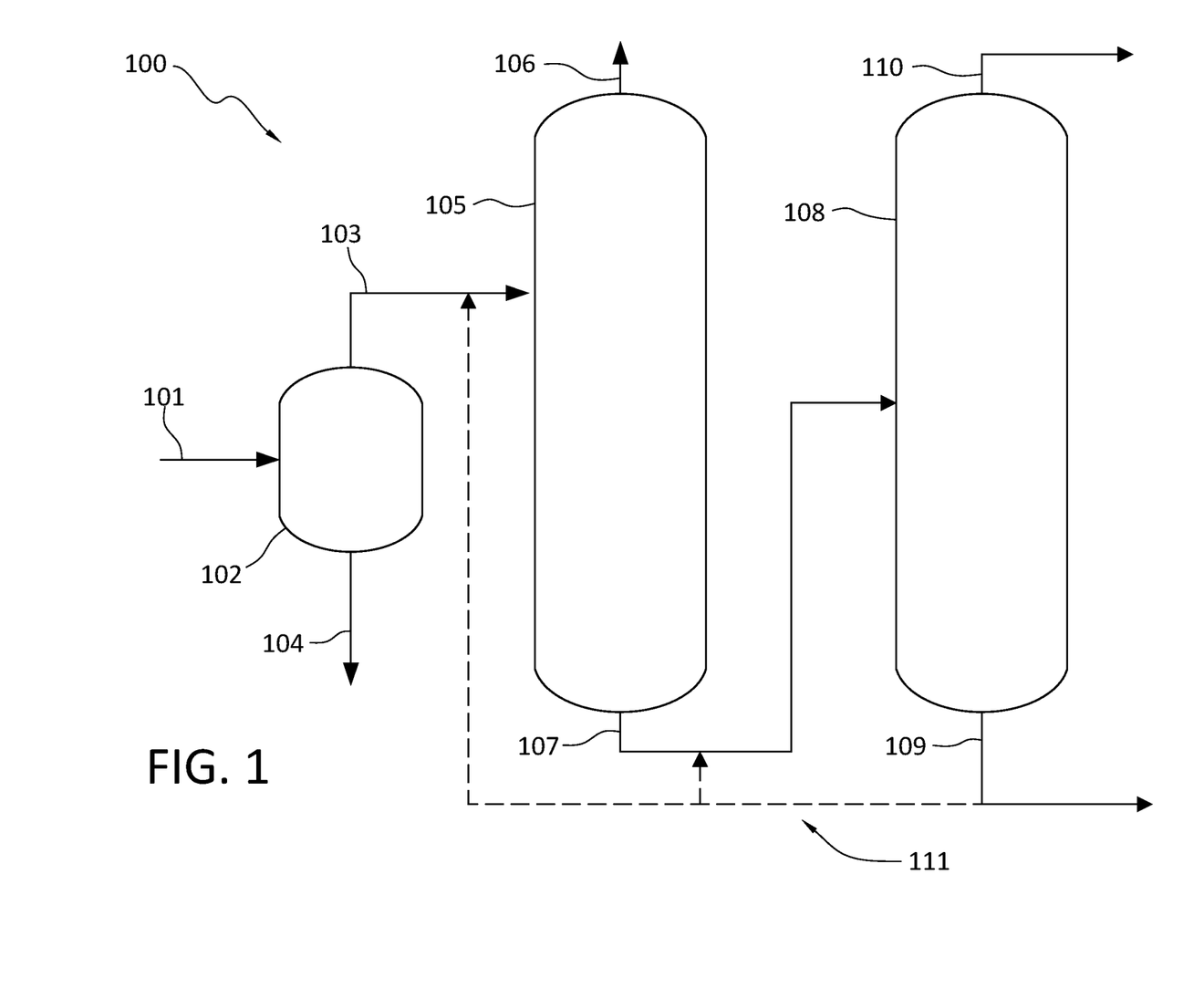
FIG. 1 depicts a schematic overview of an embodiment of the process of purifying TCH.

FIG. 1 shows one embodiment of the TCH purification process 100. In this embodiment, an adiponitrile process stream 101 is separated in a flash evaporator 102 to form a first overhead stream 103 and a first bottoms stream 104. The first overhead stream 103 is then separated in a first distillation column 105 to form a lights stream as a second overhead stream 106 and a second bottoms stream 107. The second bottoms stream is then separated in a second distillation column 108 to form a heavies stream as a third bottoms stream 109 and a TCH stream as a third overhead stream 110. This embodiment also features an optional recycle step 111, whereby a portion of the third bottoms stream 109 is recycled to the first overhead stream 103 and/or the second bottoms stream 107.

Figure 2:
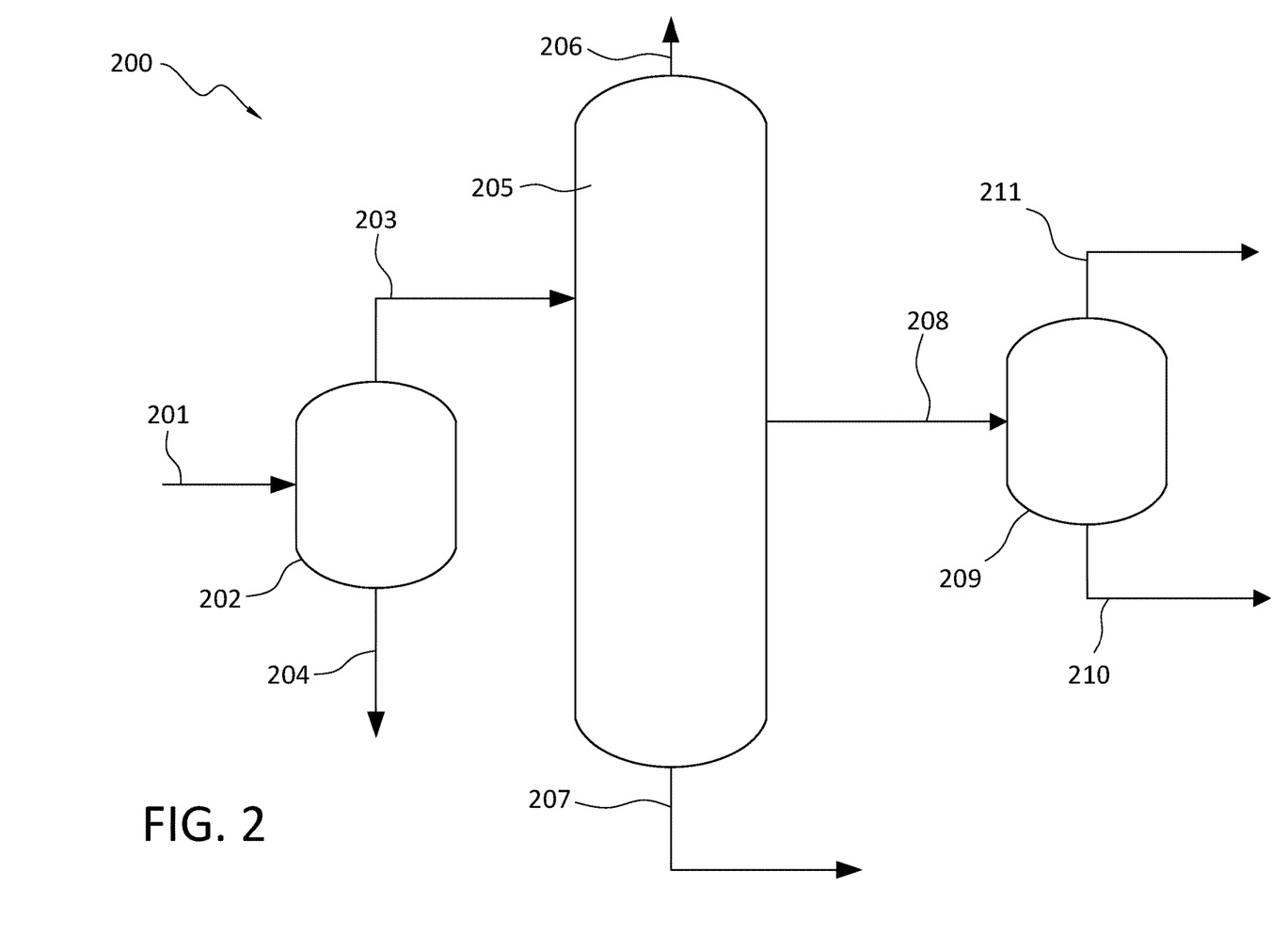
FIG. 2 depicts a schematic overview of another embodiment of the process of purifying TCH.

FIG. 2 shows another embodiment of the TCH purification process 200. In this embodiment, an adiponitrile process stream 201 is separated in a flash evaporator 202 to form a first overhead stream 203 and a first bottoms stream 204. The first overhead stream 203 is then separated in a first distillation column 205 to form a lights stream as a second overhead stream 206, a second bottoms stream 207, and a side draw 208. The side draw 208 is then separated in a flasher 209 to form a TCH stream as a third bottoms stream 210 and a third overhead stream 211.

Figure 3:
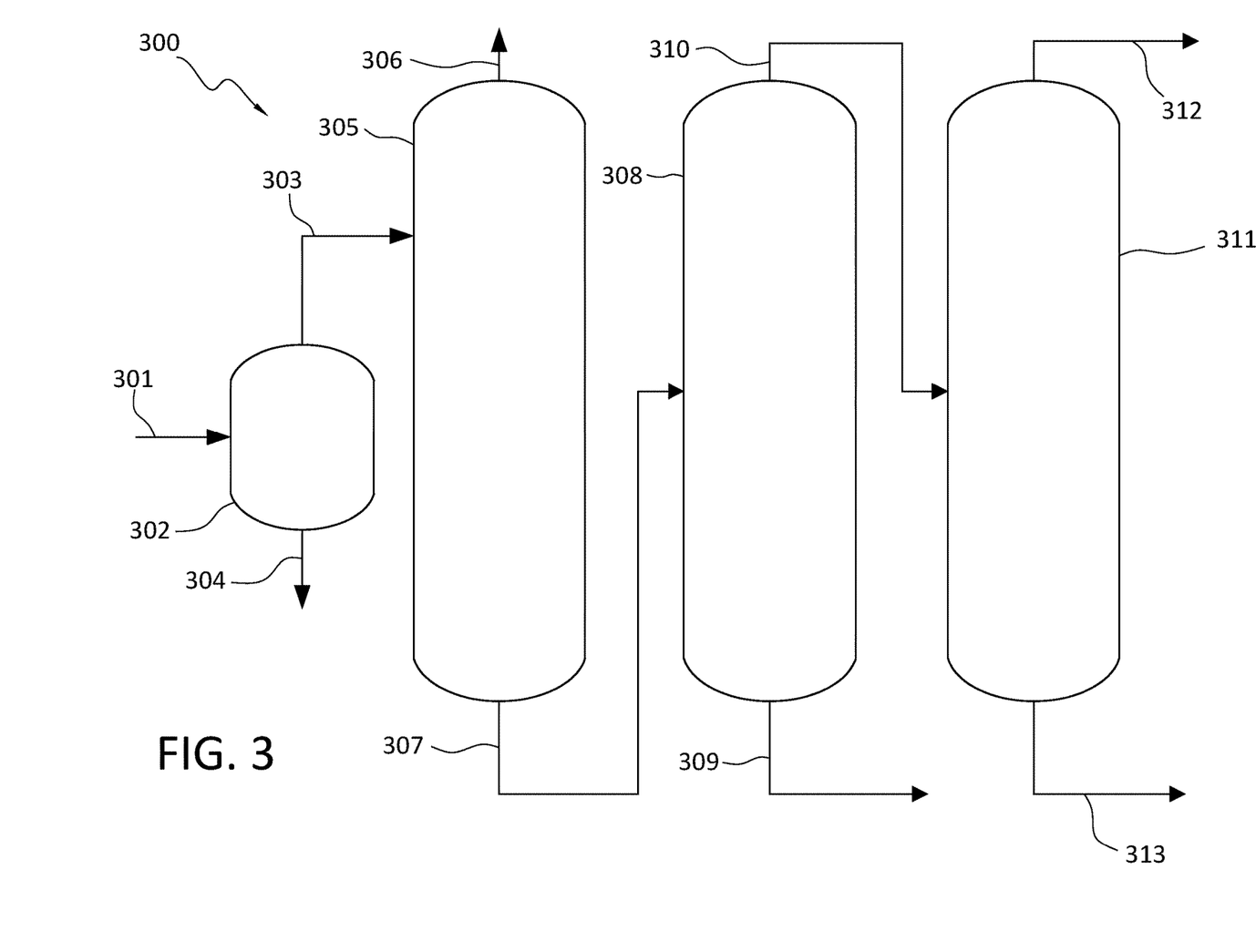
FIG. 3 depicts a schematic overview of another embodiment of the process of purifying TCH.

FIG. 3 shows another embodiment of the TCH purification process 300. In this embodiment, an adiponitrile process stream 301 is separated in a flash evaporator 302 to form a first overhead stream 303 and a first bottoms stream 304. The first overhead stream 303 is then separated in a first distillation column 305 to form a lights stream as a second overhead stream 306 and a second bottoms stream 307. The second bottoms stream 307 is then separated in a second distillation column 308 to form a heavies stream as a third bottoms stream 309 and a third overhead, or distillate, stream 310. The third overhead stream 310 is then separated in a third distillation column 311 to form a fourth overhead stream 312 and a TCH stream as a fourth bottoms stream 313.

Figure 4:
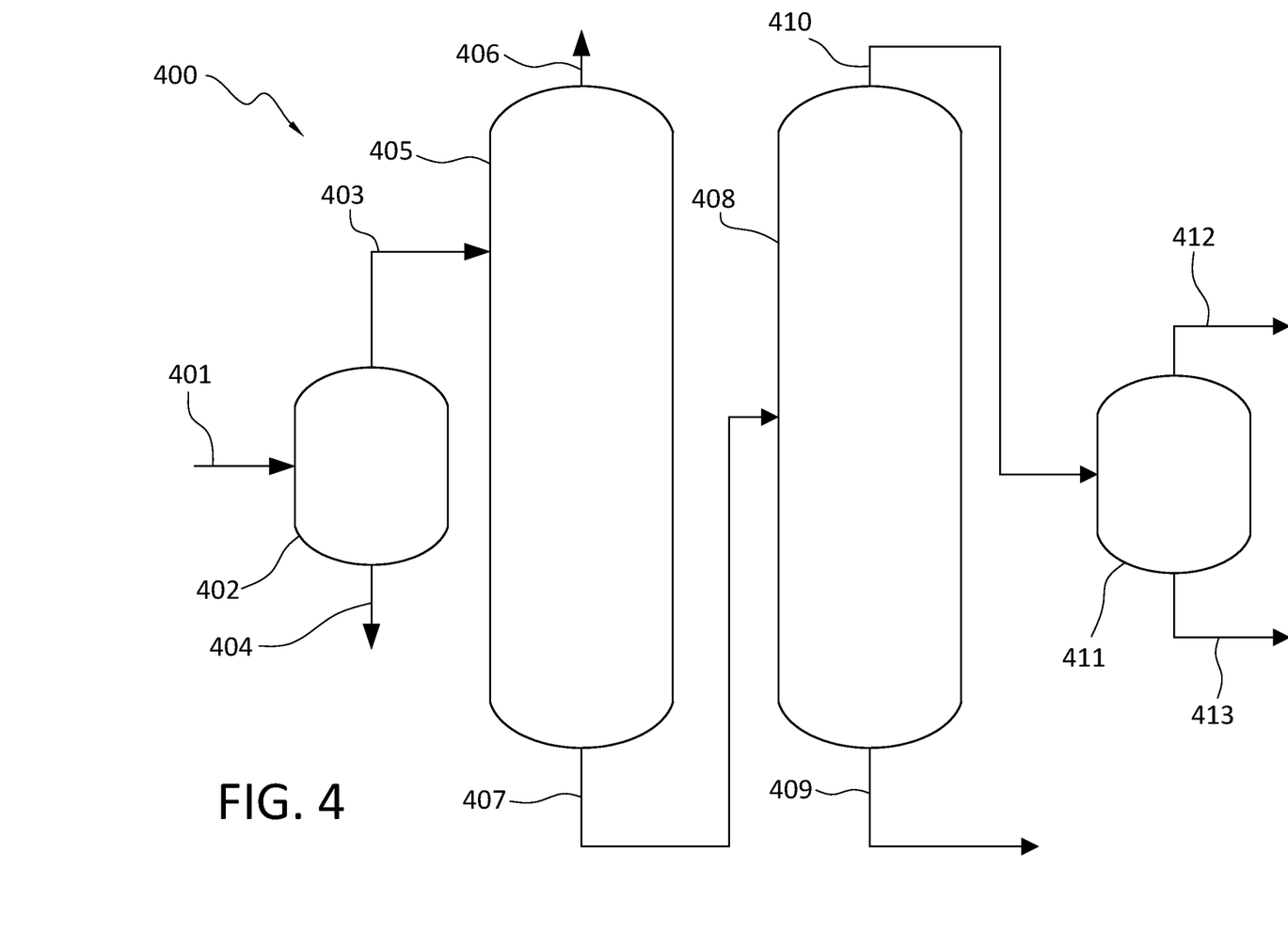
FIG. 4 depicts a schematic overview of another embodiment of the process of purifying TCH.

FIG. 4 shows another embodiment of the TCH purification process 400. In this embodiment, an adiponitrile process stream 401 is separated in a flash evaporator 402 to form a first overhead stream 403 and a first bottoms stream 404. The first overhead stream 403 is then separated in a first distillation column 405 to form a lights stream as a second overhead stream 406 and a second bottoms stream 407. The second bottoms stream 407 is then separated in a second distillation column 408 to form a heavies stream as a third bottoms stream 409 and a third overhead, or distillate, stream 410. The third overhead stream 410 is then separated in a flasher 411 to form a fourth overhead stream 412 and a TCH stream as a fourth bottoms stream 413.

Figure 5:
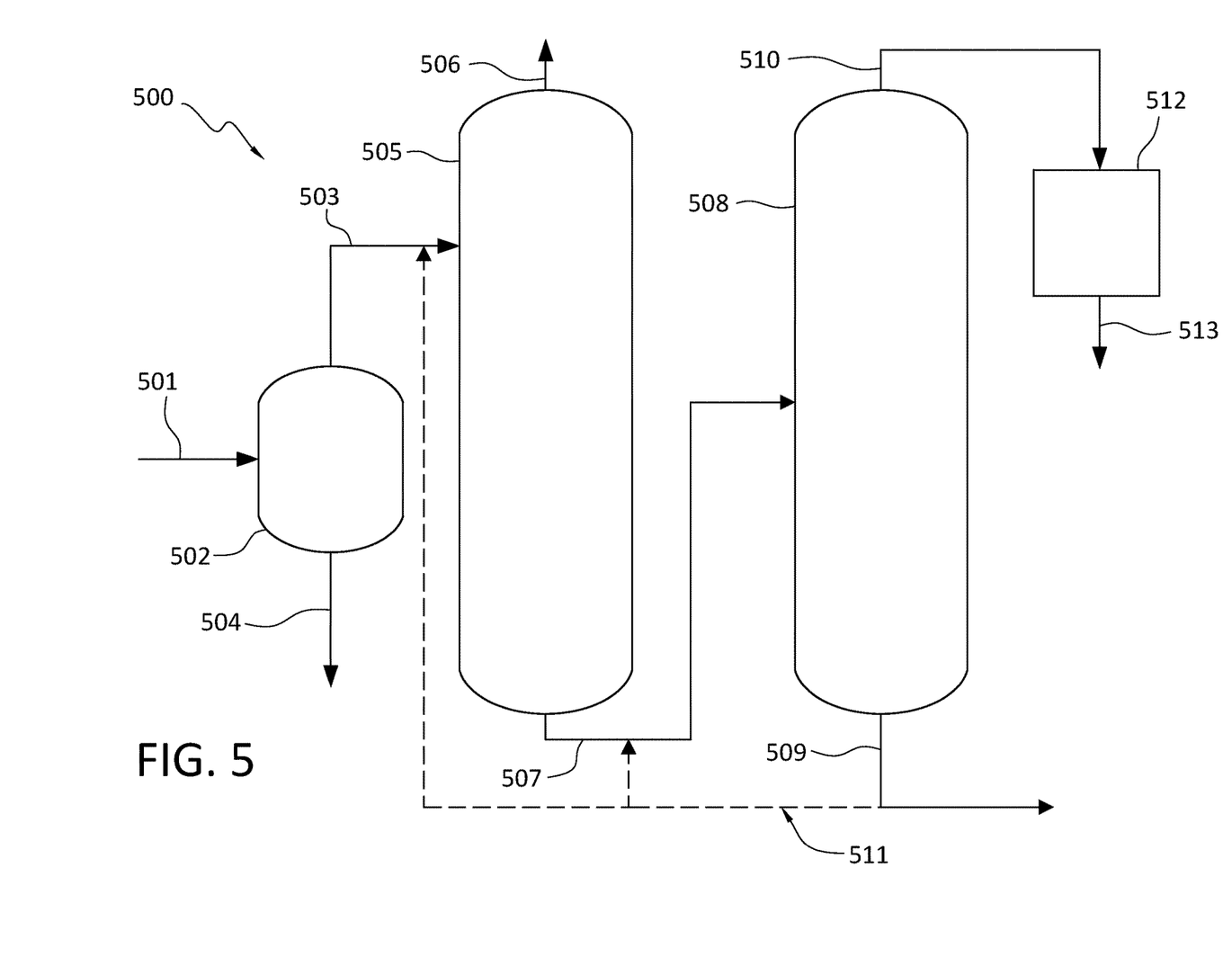
FIG. 5 depicts a schematic overview of another embodiment of the process of purifying TCH.

FIG. 5 shows another embodiment of the TCH purification process 500. In this embodiment, an adiponitrile process stream 501 is separated in a flash evaporator 502 to form a first overhead stream 503 and a first bottoms stream 504. The first overhead stream 503 is then separated in a first distillation column 505 to form a lights stream as a second overhead stream 506 and a second bottoms stream 507. The second bottoms stream 507 is then separated in a second distillation column 508 to form a heavies stream as a third bottoms stream 509 and a TCH stream as a third overhead stream 510. This embodiment also features an optional recycle step 511, whereby a portion of the third bottoms stream 509 is recycled to the first overhead stream 503 and/or the second bottoms stream 507. This embodiment also features a treating step 512, whereby the TCH stream 510 is subjected to further treatment to yield a purified TCH stream 513.

EMBODIMENTS

Embodiment 1: An embodiment of a process for purifying TCH, the process comprising: a first separating step of separating an adiponitrile process stream to form a first overhead stream comprising low-boiling components and high-boiling components and a first bottoms stream comprising high-boiling components and solid impurities; and a second separating step of separating the first overhead stream in one or more distillation columns to form a lights stream comprising low-boiling components, a heavies stream comprising high-boiling components, and a TCH stream comprising TCH and less than 10 wt. % impurities; wherein the residence time in an individual column is less than 8 hours.

Embodiment 2: The embodiment of embodiment 1, wherein the first overhead stream comprises from 0 wt. % to 20 wt. % heavies.

Embodiment 3: The embodiment of embodiment 1, wherein the TCH stream comprises less than 1 wt. % impurities.

Embodiment 4: The embodiment of embodiment 1, wherein the TCH stream comprises TCH, from 0 wt. % to 0.05 wt. % adiponitrile, from 0 wt. % to 0.1 wt. % di(2-cyanoethyl) amine, from 0 wt. % to 0.05 wt. % cyanovaleramide, and from 0 wt. % to 0.05 wt. % tri(2-cyanoethyl) amine.

Embodiment 5: The embodiment of embodiment 1, wherein the residence time of the first overhead stream in temperatures above 230° C. is less than 8 hours.

Embodiment 6: The embodiment of embodiment 1, wherein the residence time of the first overhead stream in pressures above 50 torr is less than 8 hours.

Embodiment 7: The embodiment of embodiment 1, further comprising recycling at least a portion of the heavies stream, optionally comprising from 0 wt. % to 40 wt. % high-boiling components.

Embodiment 8: The embodiment of embodiment 1, wherein the second separating step further comprises: separating the first overhead stream in a distillation column to form the lights stream as a second overhead stream and a second bottoms stream; and separating the second bottoms stream in a distillation column to form the heavies stream as a third bottoms stream and the TCH stream as a third overhead stream.

Embodiment 9: The embodiment of embodiment 8, further comprising recycling at least a portion of the third bottoms stream.

Embodiment 10: The embodiment of embodiment 9, wherein the recycling comprises recycling at least a portion of the third bottoms stream to the second bottoms stream and/or to the first overhead stream.

Embodiment 11: The embodiment of embodiment 9, wherein the recycled stream comprises from 0 wt. % to 40 wt. % high-boiling components.

Embodiment 12: The embodiment of embodiment 9, wherein the recycling controls the concentration of high-boiling components in the first overhead stream to be from 0 wt. % to 10 wt. %.

Embodiment 13: The embodiment of embodiment 1, further comprising a treating step of treating the TCH stream to form a purified TCH stream.

Embodiment 14: The embodiment of embodiment 13, wherein the treating step comprises nitrogen stripping or treating with a molecular sieve.

Embodiment 15: The embodiment of embodiment 13, wherein the purified TCH stream comprises less than 0.1 wt. % impurities, less than 20 ppm water, and/or less than 5 ppm metals.

Embodiment 16: The embodiment of embodiment 1, wherein the first separating step comprises flashing the adiponitrile stream or treating the adiponitrile stream in a wiped film evaporator.

Embodiment 17: The embodiment of embodiment 1, wherein less than 50 wt. % of high-boiling components in the first overhead stream decompose into low-boiling components during the second separating step.

Embodiment 18: The embodiment of embodiment 1, wherein the adiponitrile process stream is a co-product stream produced by an adiponitrile production and/or an adiponitrile purification process.

Embodiment 19: The embodiment of embodiment 18, wherein the first bottoms stream and/or the lights stream is recycled to the adiponitrile production and/or the adiponitrile purification process.

Embodiment 20: An embodiment of a process for purifying TCH, the process comprising: a first separating step of flashing an adiponitrile process stream to form a first overhead stream comprising low-boiling components and high-boiling components, and a first bottoms stream comprising high-boiling components and solid impurities; a second separating step of distilling the first overhead stream to form a second overhead stream comprising low-boiling components, and a second bottoms stream comprising TCH and heavies; a third separating step of distilling the second bottoms stream to form a third distillate comprising TCH and less than 5 wt.,% impurities, and a third bottoms stream comprising heavies; wherein the residence time in the second or third separating step is less than 8 hours.

Embodiment 21: The embodiment of embodiment 20, wherein at least a portion of third bottoms stream and/or the second bottoms stream is recycled.

Embodiment 22: The embodiment of embodiment 21, wherein the recycled stream comprises from 0 wt. % to 40 wt. % heavies.

Embodiment 23: An embodiment of a process for purifying TCH, the process comprising: a first separating step of flashing an adiponitrile process stream to form a first overhead stream comprising low-boiling components and high-boiling components, and a first bottoms stream comprising high-boiling components; a second separating step of distilling the first overhead stream to form a second overhead stream comprising low-boiling components, a second bottoms stream comprising heavies, and a side draw comprising TCH and lights; a third separating step of flashing the side draw in a second flash vessel to form a third bottoms stream comprising TCH and less than 5 wt % impurities wherein the residence time in the second or third separating step is less than 8 hours.

Embodiment 24: The embodiment of embodiment 23, wherein at least a portion of the second bottoms stream is recycled.

Embodiment 25: The embodiment of embodiment 24, wherein the recycled stream comprises from 0 wt % to 40 wt % heavies.

Embodiment 26: An embodiment of a process for purifying TCH, the process comprising: a first separating step of flashing an adiponitrile process stream to form a first overhead stream comprising low-boiling components and high-boiling components, and a first bottoms stream comprising high-boiling components; a second separating step of distilling the first overhead stream to form a second overhead stream comprising low-boiling components, and a second bottoms stream comprising TCH and heavies; a third separating step of distilling the second bottoms stream to form a third distillate comprising TCH and impurities, and a third bottoms stream comprising heavies; and a fourth separating step of distilling the third distillate to form a fourth overhead stream comprising low-boiling components, and a fourth bottoms stream comprising TCH and less than 5 wt. % impurities wherein the residence time in the second, third, or fourth separating step is less than 8 hours.

Embodiment 27: The embodiment of embodiment 26, wherein the fourth overhead stream comprises low-boiling components formed by the decomposition of high-boiling components during the second separating step.

Embodiment 28: The embodiment of embodiment 26, wherein at least a portion of the second, third, or fourth bottoms stream is recycled.

Embodiment 29: The embodiment of embodiment 28, wherein the recycled stream comprises from 0 wt % to 40 wt % heavies.

Embodiment 30: An embodiment of a process for purifying TCH, the process comprising: a first separating step of separating an adiponitrile process stream to form a first overhead stream comprising low-boiling components and high-boiling components, and a first bottoms stream comprising high-boiling components; a second separating step of distilling the first overhead stream to form a second overhead stream comprising low-boiling components, and a second bottoms stream comprising TCH and heavies; third separating step of distilling the second bottoms stream to form a third distillate comprising TCH and impurities, and a third bottoms stream comprising heavies; and a fourth separating step of flashing the third distillate in a second flash vessel to form a fourth overhead stream comprising low-boiling components, and a fourth bottoms stream comprising TCH and less than 5 wt. % impurities wherein the residence time in the second or third separating step is less than 8 hours.

Embodiment 31: The embodiment of embodiment 30, wherein the fourth overhead stream comprises low-boiling components formed by the decomposition of high-boiling components during the second and/or third separating step.

Embodiment 32: The embodiment of embodiment 30, wherein at least a portion of the second or third bottoms stream is recycled.

Embodiment 33: The embodiment of embodiment 32, wherein the recycled stream comprises from 0 wt. % to 40 wt. % heavies.

EXAMPLES

The present disclosure will be further understood by reference to the following non-limiting example.

Example 1

A TCH-containing feed stream was collected from an adiponitrile production and purification process. That is, the feed stream in this example was an adiponitrile process stream. The feed stream was separated in a wiped film evaporator four times. The multiple passes through the wiped film evaporator produced a first overhead stream and a first bottoms stream, which comprised high-boiling components and solid impurities. The first bottoms stream was discarded. The compositions of the feed stream first overhead stream are provided in Table 1, below.

The first overhead stream was distilled in a first distillation column. The first distillation column was operated at a column bottom temperature of about 255° C., and the residence time of the first overhead stream in the first distillation column was less than 4 hours. The first distillation column produced a second overhead stream (lights stream), which was a low-volume stream that was discarded. The first distillation column also produced a second bottoms stream, which contained a high concentration of TCH and some heavies.

The second bottoms stream was then distilled in a second distillation column. The second distillation column was operated at a column bottom temperature of about 263° C., and the residence time of the second bottoms stream in the second distillation column was less than 4 hours. The second distillation column produced a third bottoms stream (heavies stream). The heavies stream can be recycled and/or discarded. The second distillation column also produced a third overhead stream (TCH stream). The composition of the lights stream, the second bottoms stream, the heavies stream, and the TCH stream are provided in Table 2, below.

TABLE 1

| First Separating Step | | |
| --- | --- | --- |
| Component | Feed Stream | First Overhead Stream |
| Adiponitrile | 5.0 | 1.0 |
| TCH | 80.0 | 95.0 |
| Lights | 5.0 | 1.5 |
| Heavies | 10.0 | 2.5 |

TABLE 2

| Second Separating Step | | | | |
| --- | --- | --- | --- | --- |
| Component | Lights Stream | Second Bottoms Stream | Heavies Stream | TCH Stream |
| Adiponitrile | 7.1 | 0.0 | 0.0 | 0.0 |
| TCH | 80.3 | 97.4 | 90.2 | 99.2 |
| Lights | 10.6 | 0.0 | 0.0 | 0.0 |
| Heavies | 2.0 | 2.6 | 9.8 | 0.8 |

As the above tables show, the purification process carried out in Example 1 produced a highly pure TCH stream. In particular, the purification process resulted in a TCH stream comprising greater than 99 wt. % TCH and comprising no measurable adiponitrile or lights. As shown, the concentration of the heavies in the second bottoms stream and/or the heavies stream was maintained within the ranges and limits disclosed herein.

We claim:

1. A process for purifying TCH, the process comprising:
   a first separating step of separating a feed stream to form a first overhead stream comprising low-boiling components and high-boiling components and a first bottoms stream comprising high-boiling components and solid impurities; and
   a second separating step of separating the first overhead stream in one or more distillation columns to form a lights stream comprising low-boiling components, a heavies stream comprising high-boiling components, and a TCH stream comprising TCH, from 0 wt. % to 0.05 wt. % adiponitrile, from 0 wt. % to 0.1 wt. % di(2-cyanoethyl) amine, from 0 wt. % to 0.05 wt. % cyanovaleramide, and from 0 wt. % to 0.05 wt. % tri(2-cyanoethyl) amine, and less than 10 wt. % additional impurities; and
   wherein the residence time of the first overhead stream in temperatures above 230° C. in any column at any step in the process is less than 8 hours.

2. The process of claim 1, wherein the first overhead stream comprises less than 20 wt. % heavies.

3. The process of claim 1, wherein the TCH stream comprises less than 1 wt. % additional impurities.

4. The process of claim 1, wherein the residence time of the first overhead stream in pressures above 50 torr is less than 8 hours.

5. The process of claim 1, further comprising recycling at least a portion of the heavies stream.

6. The process of claim 1, wherein the second separating step further comprises:
   separating the first overhead stream in a distillation column to form the lights stream as a second overhead stream and a second bottoms stream; and
   separating the second bottoms stream in a distillation column to form the heavies stream as a third bottoms stream and the TCH stream as a third overhead stream.

7. The process of claim 6, further comprising recycling at least a portion of the third bottoms stream.

8. The process of claim 7, wherein the recycling comprises recycling at least a portion of the third bottoms stream to the second bottoms stream and/or to the first overhead stream.

9. The process of claim 7, wherein the recycled stream comprises from 0 wt. % to 40 wt. % high-boiling components.

10. The process of claim 7, wherein the recycling controls the concentration of high-boiling components in the first overhead stream to be from 0 wt. % to 10 wt. %.

11. The process of claim 1, further comprising a treating step of treating the TCH stream to form a purified TCH stream.

12. The process of claim 11, wherein the treating step comprises nitrogen stripping or treating with a molecular sieve.

13. The process of claim 11, wherein the purified TCH stream comprises less than 0.1 wt. % impurities, less than 20 ppm water, and/or less than 5 ppm metals.

14. The process of claim 1, wherein the first separating step comprises flashing the feed stream or treating the feed stream in a wiped film evaporator.

15. The process of claim 1, wherein less than 50 wt. % of high-boiling components in the first overhead stream decompose into low-boiling components during the second separating step.

16. The process of claim 1, wherein the feed stream is a co-product stream produced by an adiponitrile production and/or an adiponitrile purification process.

17. The process of claim 16, wherein the first bottoms stream and/or the lights stream is recycled to the adiponitrile production and/or the adiponitrile purification process.

* * * * *